United States Patent [19]
Kurtzberg et al.

[11] Patent Number: 5,585,919
[45] Date of Patent: Dec. 17, 1996

[54] ERROR MINIMIZATION APPARATUS AND METHOD FOR REAL-TIME SPECTRAL DECONVOLUTION OF CHEMICAL MIXTURES

[75] Inventors: Jerome M. Kurtzberg, Yorktown Heights; John S. Lew, Ossining, both of N.Y.

[73] Assignee: International Business Machines Corporation, Armonk, N.Y.

[21] Appl. No.: 325,746

[22] Filed: Oct. 19, 1994

[51] Int. Cl.$^6$ ......................................... G01J 3/28
[52] U.S. Cl. ........................... 356/300; 356/328; 364/498
[58] Field of Search .................................. 356/300, 326, 356/328; 364/498, 499

[56] References Cited

U.S. PATENT DOCUMENTS

| | | | |
|---|---|---|---|
| 4,807,148 | 2/1989 | Lacey | 364/498 |
| 4,847,792 | 7/1989 | Barna et al. | 364/552 |
| 4,885,254 | 12/1989 | Sung . | |
| 4,986,658 | 1/1991 | Kim | 356/318 |
| 5,014,217 | 5/1991 | Savage | 364/498 |
| 5,023,804 | 6/1991 | Hoult | 364/498 |
| 5,046,846 | 9/1991 | Ray et al. | 356/326 |
| 5,121,337 | 6/1992 | Brown | 364/498 |
| 5,121,338 | 6/1992 | Lodder | 364/498 |
| 5,124,932 | 6/1992 | Lodder | 364/498 |
| 5,218,299 | 6/1993 | Dunkel . | |
| 5,242,602 | 9/1993 | Richardson et al. | 356/300 |

*Primary Examiner*—F. L. Evans
*Attorney, Agent, or Firm*—Daniel P. Morris

[57] ABSTRACT

An apparatus and method are described for determining the relative concentrations of the N constituent chemical components of a chemical combination. The spectral response, $C_i$, of the composite sample is measured at M wavelengths $\lambda_i$, wherein $M \geq N$. The relative concentration of the jth constituent is $X_j$. The spectral response of the jth component at wavelength $\lambda_i$ is $A_{ij}$. the set of M equations $$0 = \sum_{j=1}^{N} A_{i,j} X_j - C_i$$

have intersections defining values of $X_j$ of which only those within the region defined by $0 \leq X_j$ are possible values of $X_j$. An error is assigned to each intersections and the intersection of minimum error defines the values of $X_j$. Such a determination is rapid. A profile of each of the relative concentration $X_j$ in the sample is readily and rapidly determined.

34 Claims, 4 Drawing Sheets

ERROR MINIMIZATION APPARATUS AND METHOD FOR REAL-TIME SPECTRAL DECONVOLUTION OF CHEMICAL MIXTURES

CROSS REFERENCE TO RELATED APPLICATIONS

U.S. application Ser. No. 08/326,101 filed on the same day herewith, entitled "Apparatus and Method for Real-Time Spectral Deconvolution of Chemical Mixtures" to Kurtzberg et al., the teaching of which is incorporated herein by reference describes an apparatus and method are described for determining the relative concentrations of the constituent chemical components of a chemical combination. The spectral response of the composite sample, measured at a number of wavelengths $\lambda_i$, is represented by a vector C. The relative concentration of the jth constituent is $X_j$, and the relative concentrations of each of the chemical constituents are represented by the vector X. The vector X can be determined from the vector C by the following matrix equation:

$$X = (A^T A)hu -1 A^T C$$

wherein the matrix A has elements $A_{ij}$, which is the spectral response of the jth component at wavelength $\lambda_i$. Since the matrix A is a predetermined set of numbers, the elements of vector X are readily determined from the above equation. Such a determination is rapid; a profile of each of the constituents $X_j$ in the same is readily and rapidly determined.

U.S. application Ser. No. 08/325,858 filed on the same day herewith, entitled "Apparatus and Method for Generating Profiles of Constituents of Chemical Mixtures" to Kurtzberg et al., the teaching of which is incorporated herein by reference describes an apparatus, system and method are described for determining profiles of the relative concentrations of N constituent chemical components of a chemical combination over a group of samples. For each sample a plurality of sets of relative concentrations is determined wherein each set has substantially the same error for corresponding to absorption spectra measured for the composite sample. A plurality of samples of the chemical combination are generated, for example, by removing parts of a surface sequentially. From amongst the plurality of sets of relative concentrations over the plurality of samples, a path of highest probability is determined from which profiles of each of the chemical components can be determined. The invention is applied to generating profiles of chemical constituents as material is received from a surface of a semiconductor chip to generate profiles as a function of depth into the sample.

FIELD OF THE INVENTION

The present invention is directed to a method, system and apparatus for deconvolving chemical mixtures into the constituent components of the chemical mixture.

BACKGROUND OF THE INVENTION

Contemporary technology offers many instances that require rapidly identifying the constituents of a chemical mixture. The chemical mixture can be a solid, a liquid or a gas. In the semiconductor industry numerous multilayered structures are made, for example on semiconductor chips or semiconductor chip packaging substrates. In order to monitor the quality of the products being fabricated, it may be necessary to determine the profile of various chemical species in the multilayer structure. This can be done by ablating away the material from the surface and analyzing the material that is ablated away. For such a process to have practical value, it is imperative that the ablating or etching away of the material be done rapidly and that the analysis of the etched or ablated material be performed rapidly.

IN the case of a chemical fabrication process for a liquid, it may be desirable to monitor continually the constituent components of the liquid formed by the process. For such monitoring to have value in practical use, it is imperative that the analysis of the liquid be done rapidly so that, as the liquid flows past the monitoring point, an analysis can be done at a closely spaced sequence of times.

As another example, in order to comply with increasingly stringent environmental standards it may be necessary to reduce pollutants emitted into the atmosphere by smokestacks of a manufacturing facility. To do this it may be necessary to monitor continually the chemical constituents of the gases emitted by a smokestack. To do this efficiently it may be necessary to determine these constituents at closely spaced times.

As another example, it may be desirable to construct apparatus that can be controlled so that it runs at peak efficiency, an illustrative example being a gasoline engine. To maximize the efficiency of such an engine, and minimize the pollutants in its exhaust emissions, it may become imperative to monitor continually the chemical constituents in the exhaust from the engine, and the chemical constituents of the fuel entering the engine, so that a feedback control mechanism from the exhaust monitoring can achieve the stated goals. Such an engine would require continually monitoring, at closely spaced intervals of time, the chemical constituents of the exhaust and of the fuel input.

Bursignies et al. U.S. Pat. No. 2,866,899 describes an electronic spectroanalysis computer, the apparatus quantitatively analyzes an infrared absorption spectrum of a multicomponent sample to provide a quantitative deconvolution, i.e., a decomposition of the complex spectrum in terms of the constituents' spectra. The technique involves integrations as shown in equations 10 and 11 of Busignies et al.; these integrations are time-consuming and therefore inefficient.

It is an object of the present invention to provide a system, method, and apparatus for providing the relative concentration of chemical constituents of a composite sample, and for doing this in small computation time, while minimizing an appropriate measure of error.

It is another object of the present invention to provide a system, method and apparatus for providing a profile of the relative concentrations of chemical constituents of a composite sample.

SUMMARY OF THE INVENTION

A broad aspect of the present invention is an apparatus for making measurements at M wavelengths $\lambda_i$, wherein i=1 to M, and for using these measurements to determine the concentrations $X_j$ of N component chemical constituents, wherein j=1 to N, in a chemical mixture using predetermined constituent spectral intensities $A_{ij}$ of the N component chemical constituents, wherein $M \geq N$. From measurements in absolute units, this invention determines the $X_j$ in mass units (e.g., grams), or if desired, when the mixture has known total mass, it determines these $X_j$ as relative concentrations (e.g., percentages.) Throughout this exposition, the word "relative" embrace both these alternatives. The apparatus includes:

means for measuring relative spectral intensities $C_i$ of the chemical mixture at wavelengths $\lambda_i$;

means for storing the $C_i$ as stored relative spectral intensities;

means for storing the $A_{ij}$ as stored predetermined relative constituent spectral intensities;

means for determining the relative concentrations $X_j$ from the stored relative spectral intensities and the stored relative constituent spectral intensities by generating a set of M surfaces (specifically, hyperplanes), each of N-1 dimensions, within a region defined by $0 \leq X_j$ for j=1 to N, these surfaces having the corresponding M equations $$0 = \sum_{j=1}^{N} A_{ij}X_j - C_i \quad \text{for } i = 1 \text{ to } M \tag{1}$$

and means for generating any desired intersection of these M surfaces;

means for determining which point in this region, with coordinates $(X_1, X_2, \ldots, X_N)$, yields a minimum value of the associated error $\epsilon$, this error being defined by Equation 2, where the $\epsilon_i$ are defined by Equation 3:

$$\epsilon = \sum_{i=1}^{M} |\epsilon_i| \tag{2}$$

$$\epsilon_i = \sum_{j=1}^{N} A_{ij}X_j - C_i \quad \text{for } i = 1 \text{ to } M \tag{3}$$

The point having the minimum error yields the relative concentrations $X_j$ of the N component chemical constituents of the chemical mixture.

Another broad aspect of the present invention is a method for determining the relative concentrations $X_j$ of component chemical constituents, wherein j=1 to N, in a chemical mixture using predetermined relative constituent spectral intensities $A_{ij}$ of the N component chemical constituents, wherein i=1 to M, and wherein $M \geq N$. This includes the step of measuring the relative spectral intensities $C_i$ of the chemical mixture at wavelengths $\lambda_i$;

storing the $C_i$ as stored relative spectral intensities;

storing the $A_{ij}$ as stored predetermined relative constituent spectral intensities;

determining the relative concentrations $X_j$ from the stored relative spectral intensities and the stored relative constituent spectral intensities by generating a set of M surfaces (hyperplanes) each of N-1 dimensions within a region defined by $0 \leq X_i$ for i=1 to N, from a set of M equations $$0 = \sum_{j=1}^{N} A_{ij}X_j - C_i \quad \text{for } i = 1 \text{ to } M \tag{4}$$

determining a set of intersections of the M surfaces within said region;

determining which point in the region yields the minimum value of the error $\epsilon$, a point having coordinates $(X_1, X_2, \ldots, X_N)$ and this error $\epsilon$ being defined by Equation 5, where the $\epsilon_i$ are defined by Equation 6:

$$\epsilon = \sum_{i=1}^{M} |\epsilon_i| \tag{5}$$

$$\epsilon_i = \sum_{j=1}^{N} A_{ij}X_j - C_i \quad \text{for } i = 1 \text{ to } M \tag{6}$$

the point having the minimum error defining the relative concentrations $X_j$ of the N component chemical constituents of the chemical mixture.

In a more particular aspect of the apparatus and method of the present invention, the relative spectral intensities $A_{ij}$ and $C_i$ are absorbance intensities which are generated by an absorbance spectrometer.

BRIEF DESCRIPTION OF THE DRAWINGS

These and other objects, features and advantages of the present invention will become apparent upon consideration of the following detailed description of the invention when read in conjunction with the drawings and figures, in which.

DETAILED DESCRIPTION

For the purpose of easily understanding the details of the present invention, it is described in terms of analyzing the chemical constituents of a semiconductor wafer. This is exemplary only and not limiting. The process of forming a semiconductor wafer on which integrated circuits are formed is well known. In such processing, the wafers are exposed to a sequence of chemical steps, heat treatments and mechanical operations. During this processing, it is generally known, from knowledge of the chemistry, what types of chemical compounds are included in the semiconductor wafer as each layer of an integrated circuit is formed. This knowledge can come from information about the chemicals which are being deposited as well as from understanding of the chemical reactions occurring at a surface, reactions which may form other chemical compounds. Thus, from this knowledge of the base processing of the semiconductor wafer, it is known that, in this wafer, there is a set of N possible chemical component constituents. In order to diagnose problems associated with the fabrication process for a semiconductor wafer, it is desirable to monitor the fabrication process so as to analyze the wafer, i.e., to determine the actual profile of each of the N chemical component constituents from the surface of the fully fabricated semiconductor device down to a depth into the substrate.

The apparatus described herein constitutes an apparatus in which such a semiconductor wafer can be placed, and in which there is a means to remove material, in sequence of time, from the surface of the substrate. The removed material is exposed with radiation and the absorption spectrum is measured. The apparatus, according to the present invention, provides a means for determining the relative concentrations of each of the N component chemical constituents contained in the sample being measured.

Figure 1:
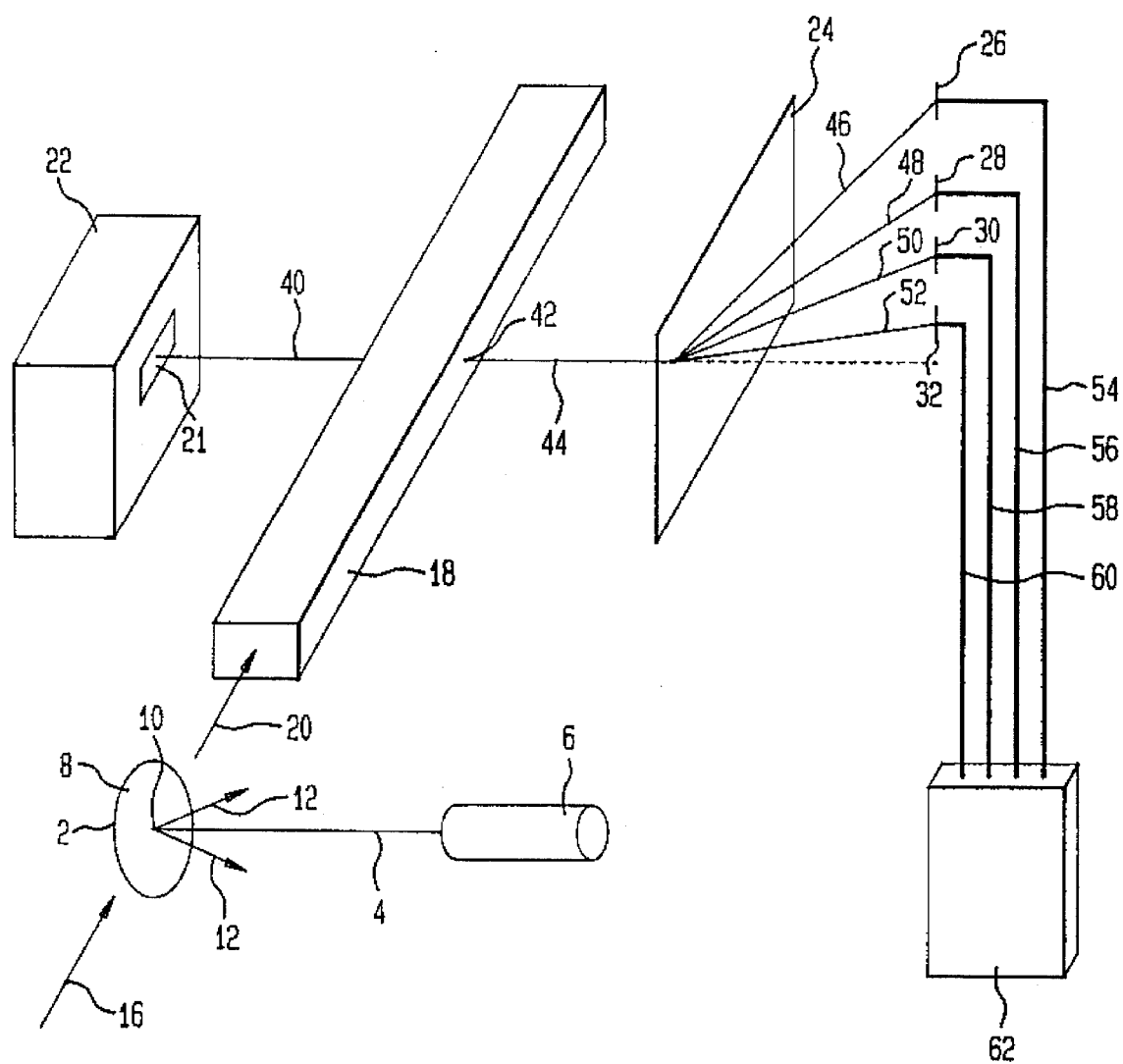
FIG. 1 is a schematic diagram of an embodiment of the apparatus according to the present invention.

FIG. 1 is a schematic diagram of an apparatus, according to the present invention, for determining profiles of chemical constituents of a semiconductor wafer 2. Wafer 2 is contained within a chamber not shown. Wafer 2 is subjected to an ion beam 4 generated by ion beam source 6. The ion beam can be any ion beam, for example, an argon ion beam. The beam 4 etches material from the surface 8 of wafer 2 at location 10, generating in the immediate vicinity of location 10 particles represented by arrows 12. An inert gas stream 16, such as an argon gas stream, carries the particles 12 into tube 18 as shown by arrow 20. Tube 20 is preferably a quartz or pyrex tube having square or rectangular cross section. Tube 18 is fed into an absorbance spectrometer, which is represented by light source 22, tube 18, grating 24 and detectors 26, 28, 30 and 32. An absorbance spectrometer useful to practice the present invention is Hewlett Packard Model 8452A Diode Array Spectrophotometer; it will be apparent to those of skill in the art how to modify such an absorbance spectrometer to practice the present invention. Light source 22 of the absorbance spectrometer has a slit through which radiation beam 40 emerges collimated and passes through tube 18 at location 42. The beam emerges as beam 44, which passes through grating 24, which splits beam 44 into beams 46, 48, 50 and 52. Each of these has a different wavelength $\lambda$ of beam 44 incident on the grating 44. Beams 46, 48, 50 and 52 are incident to detectors 26, 28, 30 and 32 respectively. Four detectors are shown for example only; in a typical apparatus there are many more detectors. Detectors 26, 28, 30 and 32 are connected by lines 54, 56, 58 and 60, respectively, to computer 62.

At period intervals of time, as different samples flow through tube 18, the relative concentrations can be redetermined to generate a profile of each $X_j$ as a function of time which can correspond to a depth into the semiconductor wafer 2. Alternatively, a group of apparatus of FIG. 1 can be arranged side by side and measurements can be made at different locations in the tube 18 to generate a profile of each $X_j$ over the spatial separation of the apparatus.

Figure 2:
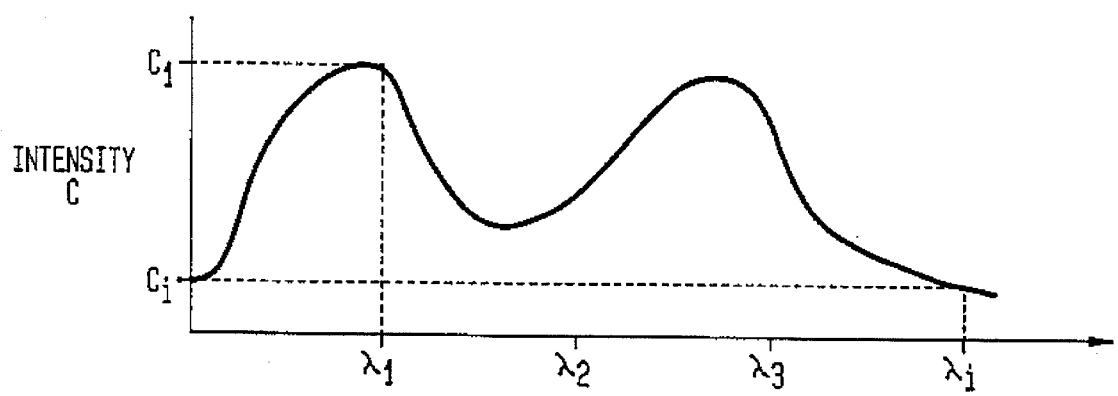
FIG. 2 is a schematic diagram of an absorption spectrum of a chemical mixture.
Figure 3:
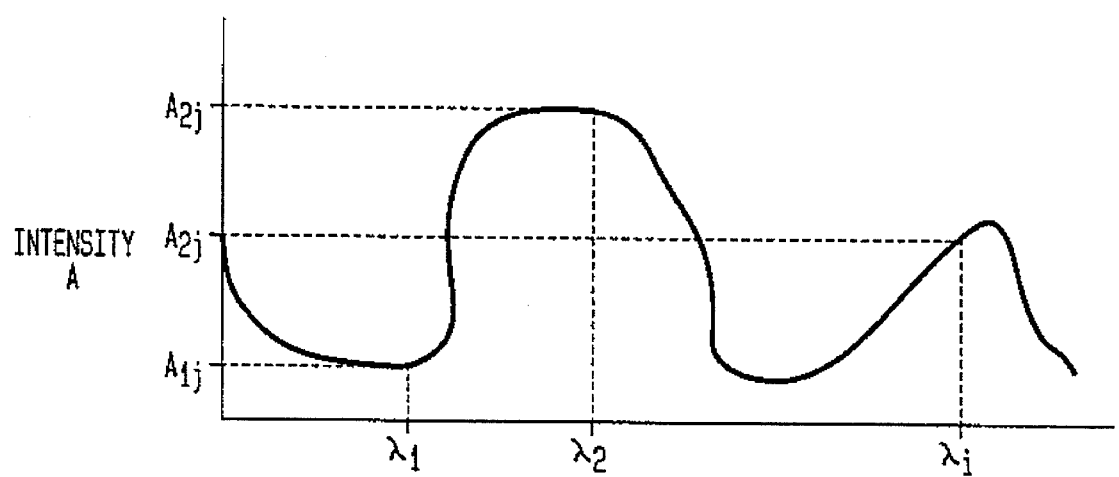
FIG. 3 is a schematic diagram of an absorption spectrum of the jth chemical constituent.

FIG. 2 is a schematic diagram of an absorption spectrum of a chemical mixture, and FIG. 3 is a schematic diagram of the jth chemical constituent.

Before gas stream 20 is permitted to flow into tube 18, beam 40 is allowed to irradiate tube 18 so that computer 62 can record an intensity at each of the detectors. This is done because for each wavelength $\lambda$ the detectors will have a different sensitivity, represented by $I_0(\lambda)$. Gas stream 20 is then permitted to flow through tube 18, next, incident beam 40 from light source 22 passes through tube 18, which contains the gas stream 20. Detectors 26, 28, 30 and 32 now measure the radiation intensity, after passing through gas stream 20, as $I(\lambda)$. If There is no absorption at a particular wavelength, the ratio of I to $I_0$ is 1. The absorption spectrum can be represented by the plot of either this ratio or its reciprocal. (The amount absorbed is proportional to 1 minus the former ratio.) The values of the most convenient ratio $R(\lambda)$ are stored in computer 20 for all values of $\lambda$.

Since it is known what are the expected chemical constituents of the gas stream 20, the absorption spectrum of each constituent is also measured and stored in computer 20. The absorption spectrum of each constituent can be measured using the Hewlett Packard Model 8452A Diode Array Spectrophotometer by inserting into the spectrophotometer a quartz or pyrex Cuvett filled with the particular chemical constituent.

A spectrum is generated as described above for each chemical constituent. Each of the j=1 to N chemical constituents is measured and the absorbance values $A_{ij}$ at wavelengths $\lambda_i$, where i=1 to M, are stored in computer 20. The absorption spectrum of the composite sample, which is comprised of at least one of the chemical constituents, is measured, and the value of the absorbance $C_i$ at $\lambda_i$ of the composite sample is stored in computer 20. The absorbance $C_i$ is equal to a linear combination of the absorbances of all the chemical constituents, wherein each chemical constituent has a concentration $X_j$, and is represented by the following equation:

$$C_i = \sum_{j=1}^{N} A_{i,j} X_j \qquad (7)$$

The value $X_j$ can be the mass of the jth constituent, or can be the fractional amount of the mass of the whole mixture if the total mass Z is a known quantity. Equation 7 can be represented in matrix form as Equation 8:

$$C = AX \qquad (8)$$

wherein C is a column vector having elements ($C_1, C_2, C_3, \ldots C_M$), wherein X is the column vector having elements ($X_1, X_2, X_3, \ldots X_n$), and wherein matrix A is a matrix of the elements $A_{ij}$. If matrix A has an inverse $A^{-1}$, then Equation 8 has a solution.

$$X = A^{-1}C \qquad (9)$$

But A has an inverse only if the matrix A is square and its rows (or equivalently columns) are linearly independent. However, in this case the resulting values of the concentrations $X_j$ will then have rather sensitive dependence on the values of the matrix elements $A_{ij}$, so that slight measurement errors in matrix elements $A_{ij}$ may generate appreciable errors in computed concentrations $X_j$.

To reduce such $X_j$ errors, it is desirable to incorporate measured values of both sample spectrum and component spectra at more wavelengths, that is, to make and use measurements at more wavelengths than there are constituent chemical components. Then M>N. Indeed, choosing M significantly larger than N admits a substantially greater amount of data sampling, which will yield a more precise determination of the concentrations $X_j$ of the chemical constituents.

But, in Equation 8, A is now no longer a square matrix. Therefore, another procedure is needed to determine the values $X_j$. In order that one may more easily understand the concept of the new procedure, this exposition describes that procedure in a simple but representative case that uses measurements at quite few wavelengths $\lambda_i$. This case assumes that one has also the total mass Z of the chemical mixture of interest. However, the procedure yields the desired values $X_j$ even when one lacks this total mass and when one uses many wavelengths.

In this special case, each mass $X_j$ must be not less than zero, and the sum of all $X_j$ must equal Z. (For example, if Z is 10 grams, then the $X_j$ will be non-negative masses whose sum is 10 grams) Thus each $X_j$ must be not greater than Z, and if a particular $X_j$ equals Z then the chemical mixture contains only the jth constituent. If Z is a known mass, then one can use Z for convenience to normalize the values $X_j$; that is, one can seek the quotients $X_j/Z$ and call these $X_1, X_2, \ldots X_n$. Then the following relations define a region of allowable values for these normalized $X_j$:

$$0 \leq X_j \leq 1 \qquad (10)$$

$$\sum_{j=1}^{N} X_j = 1 \tag{11}$$

Figure 4:
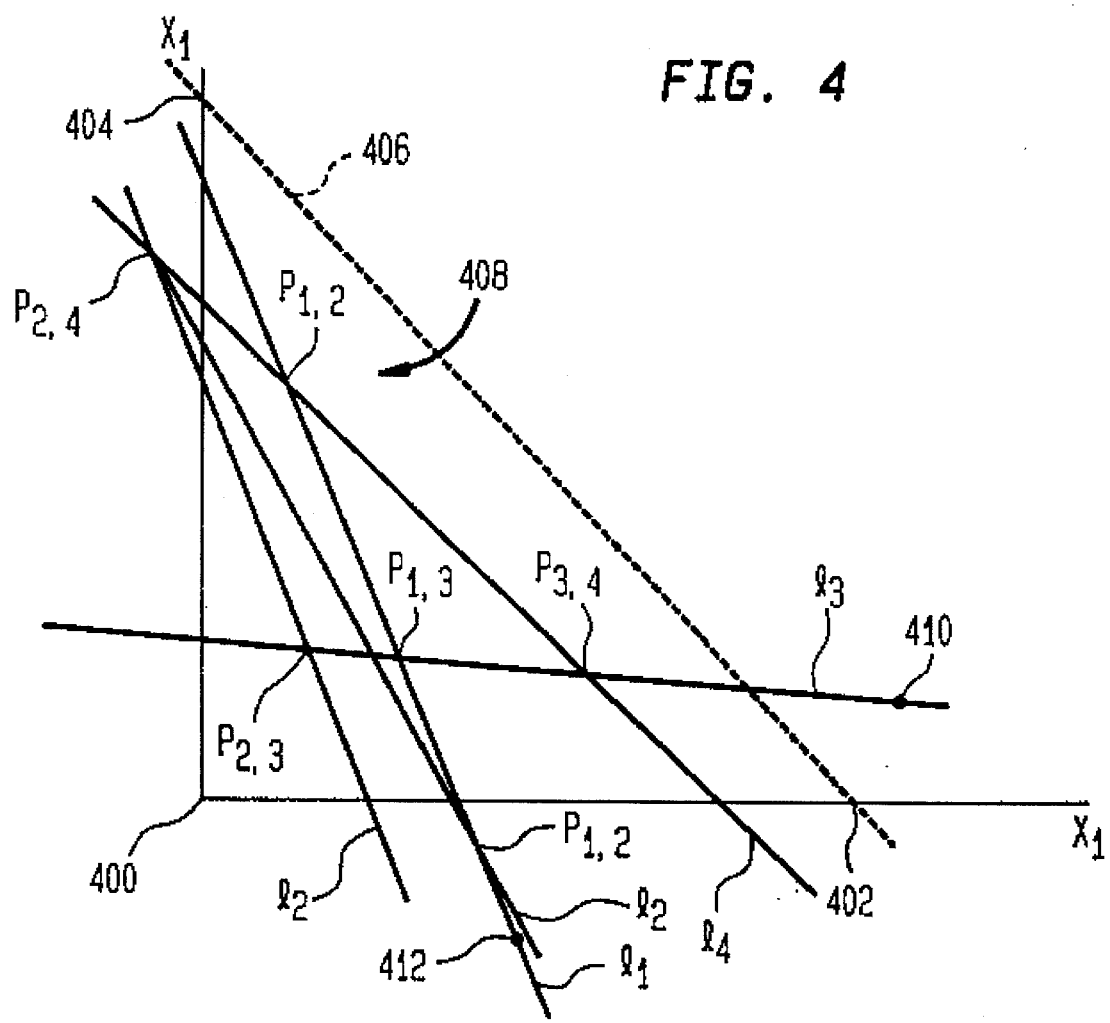
FIG. 4 shows, in a two dimensional domain of relative concentrations, intersections defining possible solutions for relative concentrations within an allowed domain for a description of a chemical mixture containing two constituents.

FIG. 4 shows an example in only two dimensions—the simplest interesting situation. There the sample mixture has just two constituents—in normalized relative amounts $X_1$ and $X_2$. By Equation 10, $X_1$ has range between 0 and 1, i.e., between points 400 and 402 in FIG. 4. Likewise, $X_2$ has range between 0 and 1, i.e., between points 400 and 404. In such two-dimensional cases, Equation 11 becomes simple Equation 12.

$$X_1 + X_2 = 1 \tag{12}$$

In FIG. 4, Equation 12 determines straight line 406 between points 402 and 404. Thus the allowed values of pairs $(X_1, X_2)$ must be points of the triangular region 408— the region whose bounds are the line 406 together with the $X_1$ and $X_2$ coordinate axes. Points outside this region, like points 410 and 412 in FIG. 4, have coordinates that are not allowed values.

In this case, where the chemical mixture has only two possible constituents, equation 7 reduces to Equation 13, which in FIG. 4 determines a straight line for each possible i wherein i=1 to M.

$$C_i = A_{i,1} X_1 + A_{i,2} X_2 \tag{13}$$

The subscript i, as described herein above, corresponds to a wavelength $\lambda$, at which the apparatus measures spectrum values. If the apparatus uses four such wavelengths $\lambda_i$, then Equation 13 determines four straight lines: $l_1, l_2, l_3,$ and $l_4$, as shown in FIG. 4. If coefficient pair $(A_{1,1}, A_{1,2})$ for line $l_1$ and corresponding pair $(A_{2,1}, A_{2,2})$ for line $l_2$ are linearly independent, that is, if $l_1$ is not parallel to $l_2$, then line $l_1$ will intersect line $l_2$ at some point which in FIG. 4 is shown as point $P_{1,2}$. Lines $l_3$ and $l_4$ are shown intersecting in point $P_{3,4}$. Lines $l_2$ and $l_3$ are shown intersecting at point $P_{2,4}$. Lines $l_2$ and $l_4$ are shown intersecting at point $P_{2,4}$. Line $l_1$ intersects line $l_2$ at point $P_{1,2}$. Line $l_1$ intersects line $l_3$ at point $P_{1,3}$. Since points $P_{2,4}$ and points $P_{1,2}$ are outside the allowed region 408, they do not represent points having allowed coordinates. This leaves points $P_{1,2}$, $P_{3,4}$, $P_{1,3}$, and $P_{2,3}$ as points of intersection within the allowed region 408.

For the lines with Equations 13, finding intersections of pairs poses merely several problems like Equation 8, where A is a square matrix; hence A has an inverse, and Equation 9 gives the solution. Thus taking lines $l_i$ two at a time and using Equation 9 on each pair yields values $X_1$ and $X_2$ which satisfy the equations for both lines $l_1$ and $l_2$. However, for the lines with Equations 13, if the intersection point of any pair is a point of the allowed region satisfying Equations 10 and 11, then this point is a candidate for best approximation to a solution of the whole Equation-set 13 for i=1 to 4. Still, from among all such intersections, some procedure must determine which provides the best set of $X_j$ values. Such a procedure needs a measure of the error. Here Equation 14 defines the error $\epsilon$ to be the sum of the absolute values of the errors $\epsilon_i$ in Equations 13 for i=1 to M. That is, $$\epsilon = \sum_{i=1}^{M} |\epsilon_i| \tag{14}$$

The errors $\epsilon_i$ of equation 14 correspond to a particular intersection point. To indicate this more clearly, rewrite Equation 14 as Equation 15:

$$\epsilon(\{X_j'\}) = \sum_{i=1}^{N} |\epsilon_i(\{X_j'\})| \tag{15}$$

That is, $\{X_j'\}$ indicates the coordinates of a particular point in one of the intersections, for example point $P_{1,2}$ of FIG. 4. The value of $\epsilon_i$ is given by Equation 16.

$$\epsilon(\{X_j'\}) = \sum_{j=1}^{N} A_{i,j} X_j' - C_i \tag{16}$$

For the simple case shown in FIG. 4, Equation 14 reduces to Equation 17.

$$\epsilon = |\epsilon_1| + |\epsilon_2| + |\epsilon_3| + |\epsilon_4| \tag{b 17}$$

Thus Equation 17 takes the following form, wherein point $P_{1,2}$ of FIG. 4 represents the coordinates $(X_1, X_2)$.

$$\epsilon(P_{1,2}) = |\epsilon_1(P_{1,2})| + |\epsilon_2(P_{1,2})| + |\epsilon_3(P_{1,2})| + |\epsilon_4(P_{1,2})| \tag{18}$$

But $\epsilon_1(P_{1,2})$ and $\epsilon_2(P_{1,2})$ are both zero, since the intersection $P_{1,2}$ is on both lines $l_1$ and $l_2$; whereas $\epsilon_3(P_{1,2})$ and $\epsilon_4(P_{1,2})$ are both non-zero, since generally the intersection $P_{1,2}$ is not on lines $l_3$ and $l_4$. These non-zero errors, $\epsilon_3$ and $\epsilon_4$, represent essentially the facts that the intersection $P_{1,2}$ is on neither line 3 nor line 4, respectively. The simples situation is shown in the two-dimensional example of FIG. 4. If the spectra are obtained at a large number of wavelengths, then the number of intersections increases significantly. From Equation 13, each wavelength generates a line; so, for example, if the number of wavelengths is 100, then there are 100 lines that can intersect. However, lines intersect in pairs, whence there are 4950 possible points of intersection in the allowed region. In the general case, there can be a large number of wavelengths, and a large number of dimensions, that is, of constituents for which values of $X_j$ are being determined. It can be shown that some intersection point minimizes the error $\epsilon$, but there can be a very large number of intersections that are possible solutions for the $X_j$ values. Thus, it is desirable that a simple procedure should determine which one of these intersections produces the minimum error.

In the general case, Equation 1 defines a set of M surfaces (hyperplanes) of dimension N-1 in an N dimensional space. These M surfaces intersect within the N dimensional space to yield the intersection points. Those points that are in the allowed region defined by Equations 10 and 11 are possible solutions for the N values of $X_j$. Which one of these intersections provides the minimum error $\epsilon$, as defined by Equation 14, is determined by linear programming. Linear programming is a technique well known in the art. In the general case Equation 7 defines a set of N-1 dimensional surfaces which intersect to define points in the N dimensional space, lines in the N dimensional space and surfaces in the N dimensional space.

The set satisfying all conditions is a polytope (generalized polyhedron) in this N dimensional space. Some vertex of this polytope is a point of minimum error. There can be more than one point which has this minimum error. Two points having the same minimum error will be connected by a line segment in the N dimensional space along which the points have the same minimum error. Indeed, there can be more than two points having the same minimum error; then these points will lie in a lower-dimensional polytope on the surface of the previously mentioned one, and all points in this lower-dimensional set will have the same minimal error.

Figure 6:
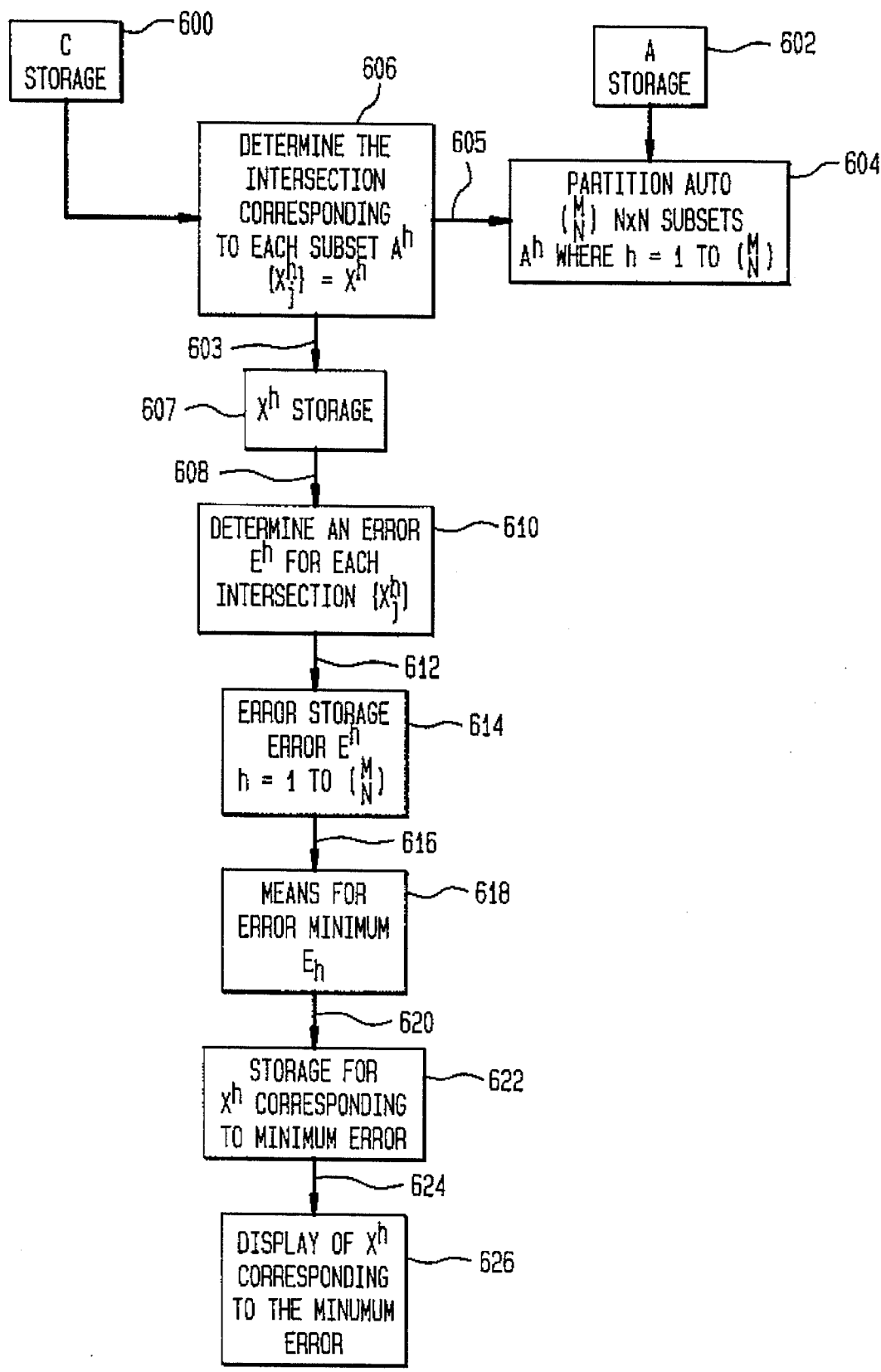
FIG. 6 is a flow chart of the method for determining the relative concentrations of chemical constituents having a minimum error.

Among other programs, the LSO package of IBM can be used to solve efficiently, via the simplex method, the incidental linear programming problems of this invention. FIG. 6 describes the computation, and labels the data storage locations. The previously measured coefficients $A_{ij}$ having been placed in A storage 602, the newly measured spectral intensities $C_i$ having been sent to C storage 600, LSO reads the data from these designated locations, computes the desired values of the $X_j$, and communicates them in any of several alternative ways.

Figure 5:
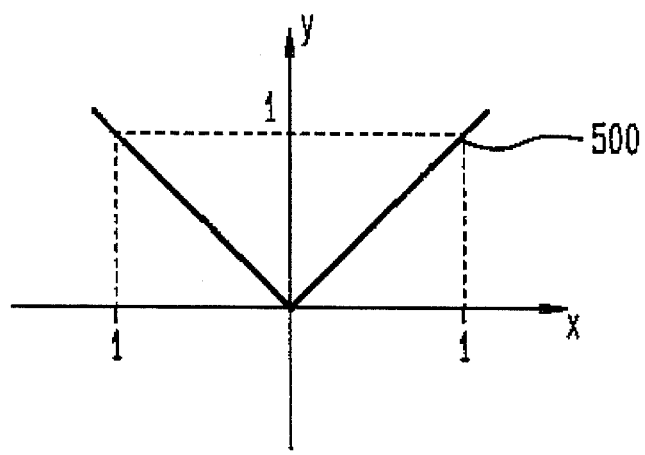
FIG. 5 shows a plot of an absolute value function.

An intersection with minimum error can be determined in more than one way. Equation 15 determines the error as the sum of the absolute value of the sub-errors $\epsilon_i$. However, the absolute value is not a linear function. Indeed, for Equation 19, FIG. 5 displays the plot as a curve 500, which is clearly not a straight line $$y = |x| \tag{19}$$

But linear programming works only with linear relations. Therefore Equation 14 cannot be used in the linear programming technique to determine the intersection having minimum error $\epsilon$. A technique is needed to introduce effectively the substance of Equation 14 by means of linear equations. This is done by replacing Equation 14 with Equation 20, wherein $u_i$ and $v_i$ are additional variables satisfying Equations 21 and 22, wherein i=1 to M.

$$\epsilon = \sum_{i=1}^{M} (u_i + v_i) \tag{20}$$

$$u_i - v_i = C_j - \sum_{j=1}^{N} A_{i,j} X_j \tag{21}$$

$$u_i \geq 0; v_i \geq 0 \tag{22}$$

Here the variables $u_i$, $v_i$, and $X_j$ can take any non-negative values, but the desired minimization forces either $u_i$ or $v_i$ to be zero for each i. Indeed, if some $u_i$ and $v_i$ satisfy Equations 21 and 22 for each i, but if neither value is zero, then for $u_i$ and $v_i$ we can substitute $$v_i' = v_i - \min(u_i, v_i), u_i' = u_i - \min(u_i, v_i) \tag{23}$$

The new values satisfy Equations 21 and 22, but decrease $\epsilon$; so, together, positive $u_i$ and $v_i$ cannot yield minimum $\epsilon$. Accordingly if, for i=1 to M, some values $u_i$ and $v_i$ yield minimum $\epsilon$, then for each pair, by Equation 20, one is zero, the other is $|\epsilon_i|$, and $$|\epsilon_i| = u_i + v_i \tag{24}$$

Hence this reformulation produces the same minimum $\epsilon$, though it involves only linear relations.

An alternative goal is to minimize a different error expression $\epsilon'$—that given by Equation 25, or equivalently, as is well known, by Equation 26.

$$\epsilon' = \max(|\epsilon_1|, \ldots, |\epsilon_M|) \tag{25}$$

$$\epsilon' = \lim_{p \to \infty} \sqrt[p]{\sum_{i=1}^{M} \left( \sum_{j=1}^{N} A_{ij} X_j - C_i \right)^p} \tag{26}$$

A slightly different trick reduces this also to a problem involving only linear relations, and thus to a problem solvable by linear programming. We add just one new variable u, defined to satisfy $$u \geq \epsilon_i, u \geq -\epsilon_i \tag{27}$$

wherein i=1 to M. This new u and the prior variables satisfy only linear relations, and we seek to minimize this u. Thus one can use linear programming to minimize $\epsilon'$ also.

FIG. 6 is an embodiment of a routine which runs on 62 of FIG. 1 to determine the best intersection point, i.e., the point giving the relative concentrations $X_j$ having minimum error $\epsilon$. The relative spectral intentions $C_i$ are stored in C storage 600. The relative constituent spectral intensities $A_{ij}$ are stored in the A storage 602. As indicated by block 604, to get an N-by-N submatrix we can choose N rows in C(M,N) ways from the M-by-N matrix $(A_{ij})$ in storage A, where $C(M,N)=M!/(N!(M-N)!)$. These submatrices we label $A^h$, where h=1 to C(M,N).

One of the submatrices $A^h$ is transferred to block 606, as indicated by line 605. At block 606 an intersection corresponding to the submatrix $A^h$ has a set of solutions $X_j$ represented by left bracket $\{X_j^j\}$, which is determined from an equation such as Equation 9. In matrix notation there is a vector $X^h$ which contains the values of the relative concentrations determined from the $A^h$ subset. As indicated by lines 608, the values of the relative concentrations $\{X^h\}$ are passed to block 610, where an error $\epsilon^h$ is determined therefor. As indicated by lines 612, this error is passed to error storage 614 which can store the most recent of the errors for h=1 to C(M,N).

A straightforward but inefficient procedure might then pass these errors, as indicated by line 616, to a means 618 for choosing the minimum of the error values $\epsilon^h$. As indicated by line 620, the values of the relative spectral intensities $X^h$ corresponding to the minimum error as passed to storage 622. The values of the relative spectral intensities $X^h$ corresponding to the minimum error can be sent, as indicated by line 624, to a display device indicated by block 626. The display device can be a printout, or can be a visual display on a terminal, such as a plot, or the like.

However, the preferred embodiment of the minimization, namely, the simplex method of linear programming, greatly shortens the search, since usually it obtains the intersection point of minimum error $\epsilon$ while determining only a small subset of all $X^h$ and the corresponding errors. That is, a starting procedure obtains one intersection point $X^h$, and then the method traverses some other intersection points and reaches the minimum-error point without calculating all the others. When the simplex method, in its progress, reaches any intersection point $X^h$, an appropriate storage unit contains a tableau of relevant numerical values. Then a so-called "pivot step" replaces this tableau by the corresponding tableau for an adjacent intersection having smaller error. Succeeding pivot steps further reduce the error until the tableau indicates that no possible step can achieve less error.

Among other programs, the LSO package of IBM can be used to solve efficiently, via the simplex method, the incidental linear programming problems of this invention. FIG. 6 describes the computation, and labels the data storage locations. The previously measured coefficients $A_{ij}$ having been placed in A storage 602, the newly measured spectral intensities $C_i$ having been sent to C storage 600, LSO reads the data from these designated locations, computes the desired values of the $X_j$, and communicates them in any of several alternative ways.

While the present invention has been shown and described with respect to specific embodiments, it should be understood that it is not thus limited. Numerous modifications, changes, and improvements will occur which fall within the scope and spirit of the invention.

We claim:

1. An apparatus for measuring relative spectral intensities $C_i$ at M wavelengths $\lambda_i$, wherein i=1 to M and for using these measurements to determine relative concentrations $X_j$ of N component chemical constituents, wherein j=1 to N, in a chemical combination using predetermined relative constituent spectral intensities $A_{ij}$ of said component chemical constituents, wherein $M \geq N$, comprising:

means for measuring relative spectral intensities $C_i$ of said chemical combination at said wavelengths $\lambda_i$;

means for storing said $C_i$ as stored relative spectral intensities;

means for storing said $A_{ij}$ as stored predetermined relative constituent spectral intensities;

means for determining said relative concentrations $X_j$ from said stored relative spectral intensities and said stored relative constituent spectral intensities;

means for generating a set of M surfaces each of N-1 dimensions within a region defined by $0 \leq X_j$ for $j=1$ to N from a set of M equations $$0 = \sum_{j=1}^{N} A_{i,j}X_j - C_i \text{ for } i = 1 \text{ to } M$$

means for determining a set of intersections of said M surfaces within said region;

means for assigning an error indicating how good said intersection is for said value of said relative concentrations;

means for storing said error;

means for determining which of said intersection has a minimum value of said error, said intersection having said minimum error defining said relative concentrations $X_j$ of said component chemical constituents of said chemical combination.

2. An apparatus according to claim 1, wherein said relative spectral intensities $A_{ij}$ and $C_i$ are absorbance intensities.

3. An apparatus according to claim 1, wherein said means for measuring said relative spectral intensities $C_i$ is an absorbance spectrometer.

4. An apparatus according to claim 1, wherein said predetermined relative spectral intensities $A_{ij}$ are determined using an absorbance spectrometer.

5. An apparatus according to claim 1, wherein said means for determining is a digital computer.

6. An apparatus according to claim 5, wherein said predetermined relative spectral intensities $A_{ij}$ are stored in said digital computer.

7. An apparatus according to claim 5, wherein said relative spectral intensities $C_i$ are stored in said computer.

8. An apparatus according to claim 1, further including a means for generating said relative spectral intensities $C_i$ at a plurality of periodic intervals in time.

9. An apparatus according to claim 8, wherein said interval of time is less than a millisecond.

10. An apparatus according to claim 1, wherein said chemical combination is selected from the group consisting of a solid, a liquid and a gas.

11. An apparatus according to claim 8, wherein said chemical combination is a solid, and further including a means for removing a portion of material at a surface of said solid, said chemical combination being said portion at each of said plurality of said time intervals, said relative concentration $X_j$ of said chemical constituent being generated for each of said time intervals, said time interval corresponding to a depth into said surface, further including a means for generating a profile of at least one of said relative concentrations $X_j$ versus said depth.

12. An apparatus according to claim 1, wherein each of said intersections has an error $\epsilon$, wherein $$\epsilon = \sum_{i=1}^{M} \left| \sum_{j=1}^{N} A_{i,j}X_j - C_i \right|$$

wherein $X_j'$ is the value of $X_j$ at said intersection.

13. An apparatus according to claim 1, wherein each of said intersection has an error $\epsilon$, wherein equivalently $$\epsilon = \max(|\epsilon_1|, \ldots, |\epsilon_M|)$$

$$\epsilon = \lim_{p \to \infty} \sqrt[p]{\sum_{i=1}^{M} \left( \sum_{j=1}^{N} A_{i,j}X_j - C_i \right)^p}$$

wherein $X_j'$ is the value of $X_j$ at said intersection.

14. An apparatus according to claim 1, further including a means for generating said relative spectral intensities $C_i$ at a plurality of samples of said chemical combination.

15. An apparatus according to claim 14, wherein said plurality of samples are spaced at periodic intervals of time and wherein profiles of at least one of said relative concentrations $X_j$ are generated versus said periodic intervals of time.

16. An apparatus according to claim 14, wherein said plurality of samples are spaced at periodic spatial intervals and wherein profiles of at least one of said relative concentrations are generated versus said periodic spatial intervals.

17. An apparatus for determining, at periodic intervals of time, the relative concentrations $X_j$ of component chemical constituents, wherein $j=1$ to N, in a chemical combination using predetermined relative constituent spectral intensities $A_{ij}$ of said N component chemical constituents, wherein $i=1$ to M, wherein $M \geq N$, comprising:

means for measuring relative spectral intensities $C_i$ of said chemical combination at wavelengths $\lambda_i$ at said periodic intervals of time;

means for storing said $C_i$ as stored relative spectral intensities;

means for storing said $A_{ij}$ as stored predetermined relative constituent spectral intensities;

means for determining said relative concentrations $X_j$ from said stored relative spectral intensities and from said stored relative constituent spectral intensities;

by generating a set of M surfaces each of N-1 dimensions within a region defined by $0 \leq X_j$ for $j=1$ to N from a set of M equations $$0 = \sum_{j=1}^{N} A_{i,j}X_j - C_i \text{ for } i = 1 \text{ to } M$$

determining a set of intersections of said M surfaces within said region;

means for assigning an error to each of said intersections indicating how good said intersection is for said value of said relative concentrations;

means for storing said error;

means for determining which of said intersections has a minimum value of said error, said intersection having said minimum error defining said relative concentrations $X_j$ of said N component chemical constituents of said chemical combination;

an electromagnetic radiation source for providing an incident beam containing said $\lambda_i$, said beam having an intensity $I_0(\lambda_i)$ at each of said $\lambda_i$;

a container through which said chemical mixture passes, said container being transparent to said $\lambda_i$;

a means for directing said incident beam at said container through which said beam passes as a transported beam;

means for measuring each of said $I_0(\lambda_i)$;

means for measuring an intensity $I(\lambda_i)$ of said transported beam at each of said $\lambda_i$;

means for comparing $I_0(\lambda_i)$ and $I(\lambda_i)$ for each of said $\lambda_i$ to determine each of said $C_i$;

means for generating a profile of at least one of said relative concentrations $X_j$ versus said periodic intervals of time.

18. A method for determining the relative concentrations $X_j$ of N component chemical constituents, wherein j=1 to N, in a chemical combination using predetermined relative constituent spectral intensities $A_{ij}$ of said N component chemical constituents, wherein i=1 to M, wherein M≥N, comprising the steps of:

measuring relative spectral intensities $C_i$ of said chemical combination at wavelengths $\lambda_i$;

storing said $C_i$ as stored relative spectral intensities;

storing said $A_{ij}$ as stored predetermined relative constituent spectral intensities;

generating a set of M surfaces each of N-1 dimensions within a region defined by $0 \leq X_j$ for j=1 to N from a set of M equations $$0 = \sum_{j=1}^{N} A_{i,j}X_j - C_i \text{ for } i = 1 \text{ to } M$$

determining a set of intersections of said M surfaces within said region;

means for assigning an error to each of said intersections indicating how good said intersection is for said value of said relative concentrations;

means for storing said error;

determining which of said intersections has a minimum value of said error, said intersection having said minimum error defining said relative concentrations $X_j$ of said N component chemical constituents of said chemical combination.

19. A method according to claim 18, wherein said relative spectral intensities $A_{ij}$ and $C_i$ are absorbance intensities.

20. A method according to claim 18, wherein said step of measuring said relative spectral intensities $C_i$ is done using an absorbance spectrometer.

21. A method according to claim 18, wherein said predetermined relative spectral intensities $A_{ij}$ are determined using an absorbance spectrometer.

22. A method according to claim 18, wherein said step of determining a set of intersections and said step of determining which of said intersections has a minimum value of said error are done using a computer.

23. A method according to claim 22, wherein said predetermined relative spectral intensities $A_{ij}$ are stored in said computer.

24. A method according to claim 22, wherein said relative spectral intensities are stored in said computer, said particular $X_j$ is set equal to zero.

25. A method according to claim 18, further including a step of generating said relative spectral intensities $C_i$ at a plurality of periodic intervals in time.

26. A method according to claim 25, wherein said interval of time is less than a millisecond.

27. A method according to claim 18, wherein said chemical combination is selected from the group consisting of a solid, a liquid and a gas.

28. A method according to claim 25, wherein said chemical combination is a solid, and further including a step for removing a portion of material at a surface of said solid, said chemical mixture being said portion at each of said plurality of said periodic intervals in time, said relative concentrations $X_j$ being generated for each of said time intervals, said time interval corresponding to a depth into said surface, further including a step of generating a profile of at least one of said relative concentrations $X_j$ versus said depth.

29. A method according to claim 18, wherein each of said intersections has an error $\epsilon$, wherein $$\epsilon = \sum_{i=1}^{M} \left| \sum_{j=1}^{N} A_{i,j}X' - C_i \right|$$

wherein x' is the value of $X_j$ at said intersection.

30. A method according to claim 18, wherein each of said intersections has an error, $\epsilon$, wherein, equivalently, $$\epsilon = \max(|\epsilon_1|, \ldots, |\epsilon_M|)$$

$$\epsilon = \lim_{p \to \infty} \sqrt[p]{\sum_{i=1}^{M} \left( \sum_{j=1}^{N} A_{i,j}X'_j - C_i \right)^p}$$

wherein $X'_j$ is the value of $X_j$ at said intersection.

31. A method according to claim 18 further including generating said relative spectral intensities $C_i$ at a plurality of samples of said chemical combination.

32. A method according to claim 31, wherein said plurality of samples are spaced at periodic intervals of time and wherein profiles of at least one of said relative concentrations $X_j$ are generated versus said periodic intervals of time.

33. A method according to claim 32, wherein said plurality of samples are spaced at periodic spatial intervals and wherein profiles of at least one of said relative concentrations are generated versus said periodic spatial intervals.

34. A method for determining, at periodic intervals of time, the relative concentrations $X_j$ of N component chemical constituents, wherein j=1 to N, in a chemical mixture using predetermined relative constituent spectral intensities $A_{ij}$ of said N component chemical constituents, wherein i=1 to M, wherein M≥N, comprising:

measuring relative spectral intensities $C_i$ of said chemical mixture at wavelengths $\lambda_i$ at said periodic intervals of time;

storing said $C_i$ as stored relative spectral intensities;

storing said $A_{ij}$ as stored predetermined relative constituent spectral intensities;

determining said relative concentrations $X_j$ from said stored relative spectral intensities and from said stored relative constituent spectral intensities;

generating a set of M surfaces each of N-1 dimensions within a region defined by $0 \leq X_j$ for j=1 to N from a set of M equations $$0 = \sum_{j=1}^{N} A_{i,j}X_j - C_i \text{ for } i = 1 \text{ to } M$$

determining a set of intersections of said M surfaces within said region;

each point within each of said intersections has coordinating $X'_j$ for j=1 to N;

assigning an error to each of said intersections indicating how good said intersection is for said value of said relative concentrations;

means for storing said error;

determining which of said intersections has a minimum value of said error, said point having said minimum error defining said relative concentrations $X_j$ of said component chemical constituents of said chemical mixture;

providing an incident electromagnetic beam containing said $\lambda_i$, said beam having an intensity $I_0(\lambda_i)$ at each of said $\lambda_i$;

passing said chemical combination through an enclosure, said enclosure being transparent to said $\lambda_i$;

directing said incident beam at said enclosure through which said beam passes as a transported beam;

measuring each of said $I_0(\lambda i)$;

measuring the intensity $I(\lambda i)$ of the transported beam at each of said $\lambda_i$;

comparing $I_0(\lambda_i)$ and $I(\lambda_i)$ to determine each of said $C_i$;

generating a profile of an least one of said relative concentrations $X_j$ versus said periodic intervals of time.

* * * * *